United States Patent
Parodi

(12) 
(10) Patent No.: US 6,206,868 B1
(45) Date of Patent: Mar. 27, 2001

(54) PROTECTIVE DEVICE AND METHOD AGAINST EMBOLIZATION DURING TREATMENT OF CAROTID ARTERY DISEASE

(75) Inventor: Juan Carlos Parodi, Ciudad de Buenos Aires (AR)

(73) Assignee: Arteria Medical Science, Inc., San Francisco, CA (US)

( * ) Notice: Subject to any disclaimer, the term of this patent is extended or adjusted under 35 U.S.C. 154(b) by 0 days.

(21) Appl. No.: 09/333,074

(22) Filed: Jun. 14, 1999

Related U.S. Application Data

(63) Continuation-in-part of application No. PCT/US99/05469, filed on Mar. 12, 1999, which is a continuation-in-part of application No. 09/078,263, filed on May 13, 1998.

(30) Foreign Application Priority Data

Mar. 12, 1999 (AR) .......................................... P 98 01 01146

(51) Int. Cl.⁷ .................................................. A61M 31/00
(52) U.S. Cl. ............................................ 604/500; 604/509
(58) Field of Search ..................................... 606/200, 191, 606/194, 195; 604/509, 500, 101.01

(56) References Cited

U.S. PATENT DOCUMENTS

| 4,794,928 | 1/1989 | Kletschka ............................. 128/344 |
| 4,921,478 | 5/1990 | Solano et al. ......................... 604/53 |
| 5,549,626 | * 8/1996 | Miller et al. ........................ 606/200 |
| 5,833,650 | * 11/1998 | Imran .................................... 604/96 |
| 6,013,085 | * 1/2000 | Howard ................................ 606/108 |

FOREIGN PATENT DOCUMENTS

| 0 427 429 A2 | 5/1991 | (EP) ............................. A61M/25/10 |

* cited by examiner

Primary Examiner—Sharon Kennedy
Assistant Examiner—Kevin C. Sirmons
(74) Attorney, Agent, or Firm—Fish & Neave; Nicola A. Pisano

(57) ABSTRACT

Methods and apparatus are provided for removing emboli during an angioplasty, stenting or surgical procedure using a catheter having an occlusion element disposed on its distal end, a suction device, and an aspiration lumen communicating therebetween. The occlusion element is configured to be placed proximal of a stenosis and deployed to occlude antegrade flow, so that flow is reversed in the vessel when the suction device is selectively activated. The aspiration lumen is sized so that an interventional device, such as an angioplasty catheter, may be readily advanced therethrough to the site of a stenosis. The suction device may be activated intermittently at key stages of the procedure to provide reverse flow through the vessel, and the catheter may include bypass holes for limiting suction levels and/or providing intermittent antegrade flow.

10 Claims, 7 Drawing Sheets

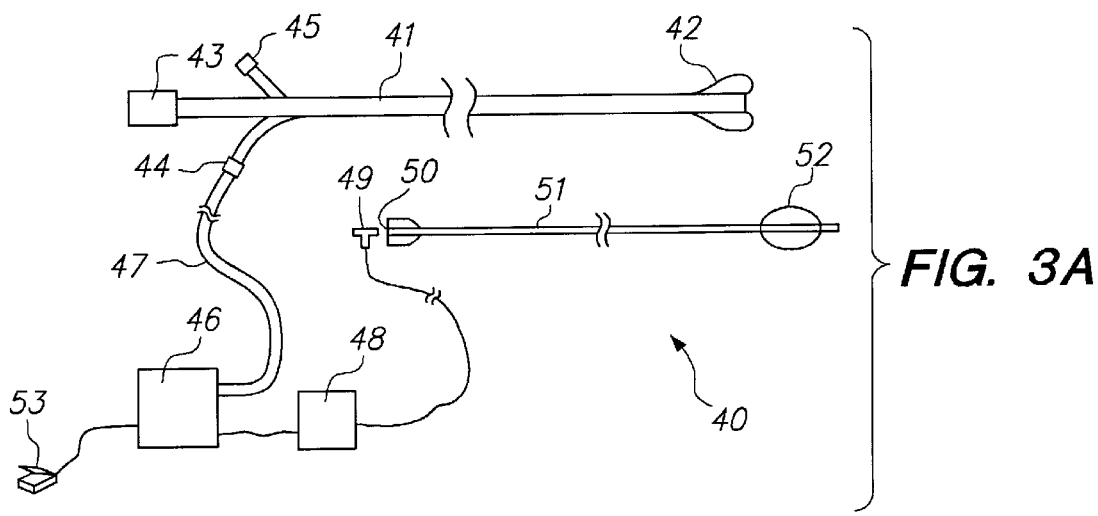
FIG. 3A
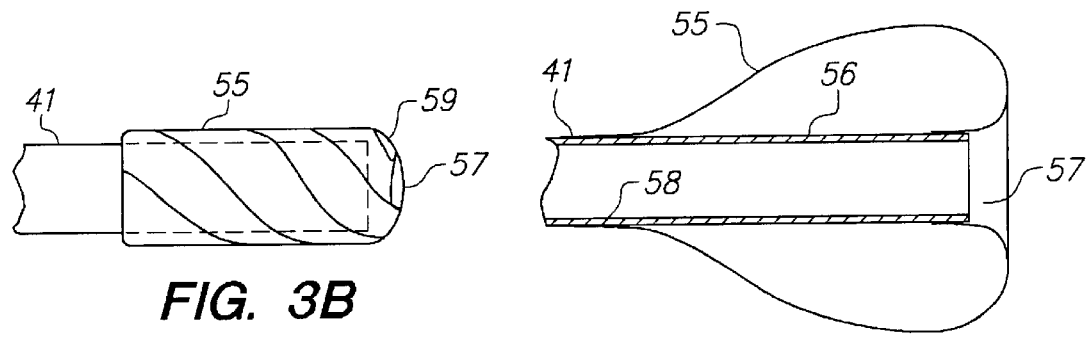
FIG. 3B
FIG. 3C
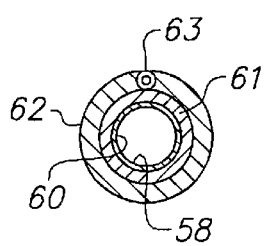
FIG. 3D
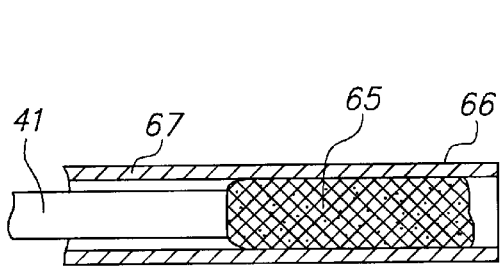
FIG. 4A
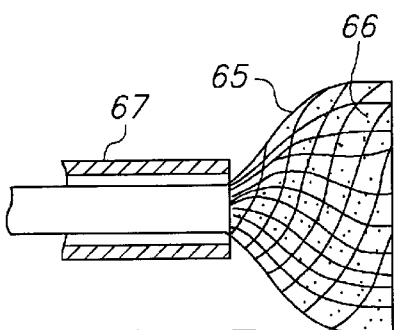
FIG. 4B

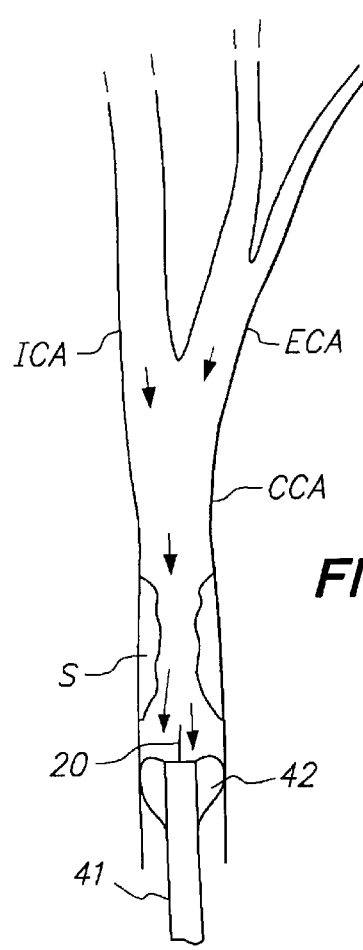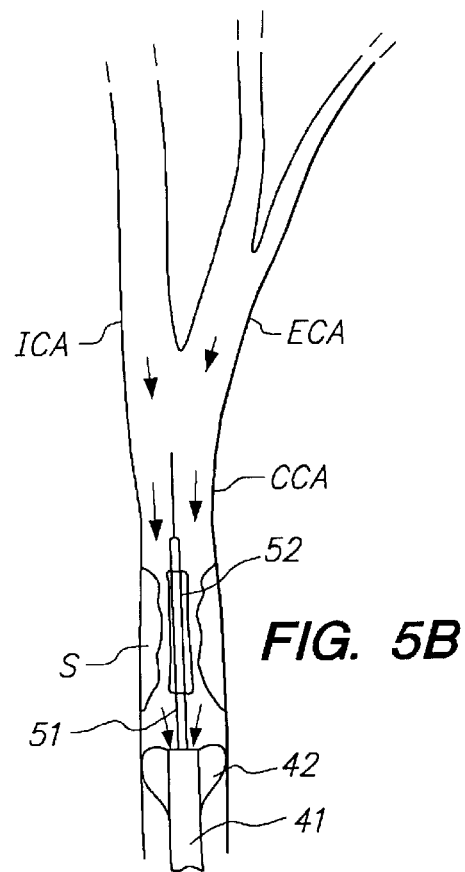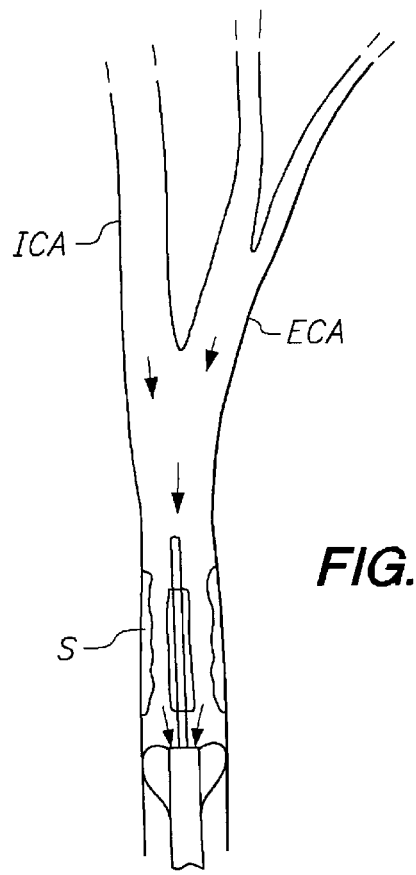

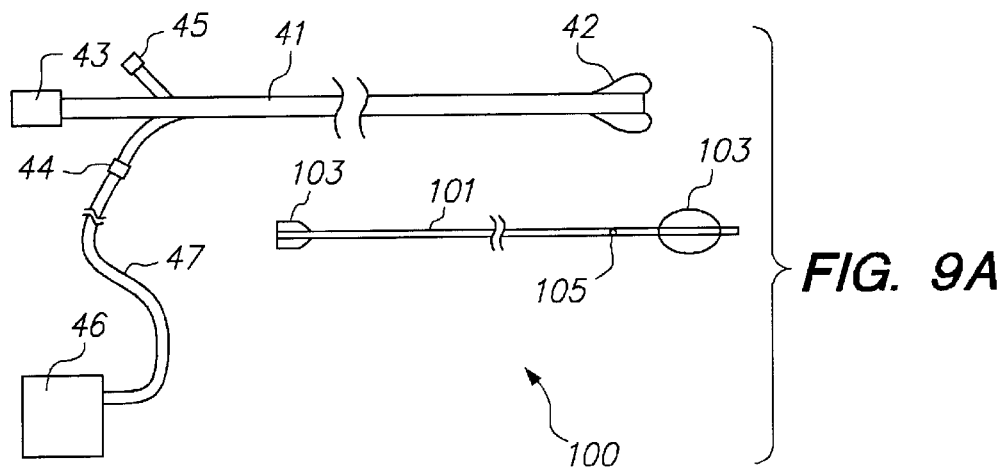
*FIG. 9A*
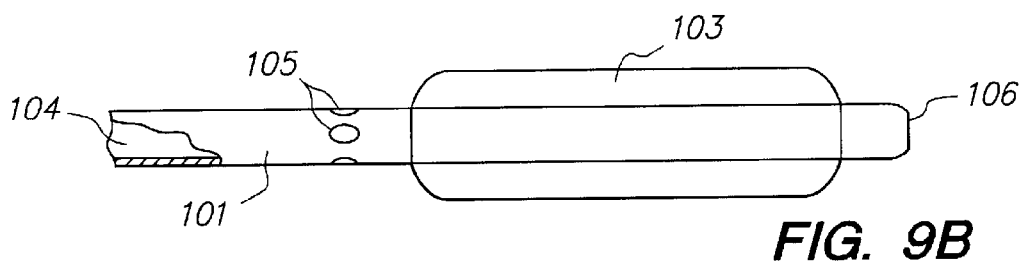
*FIG. 9B*
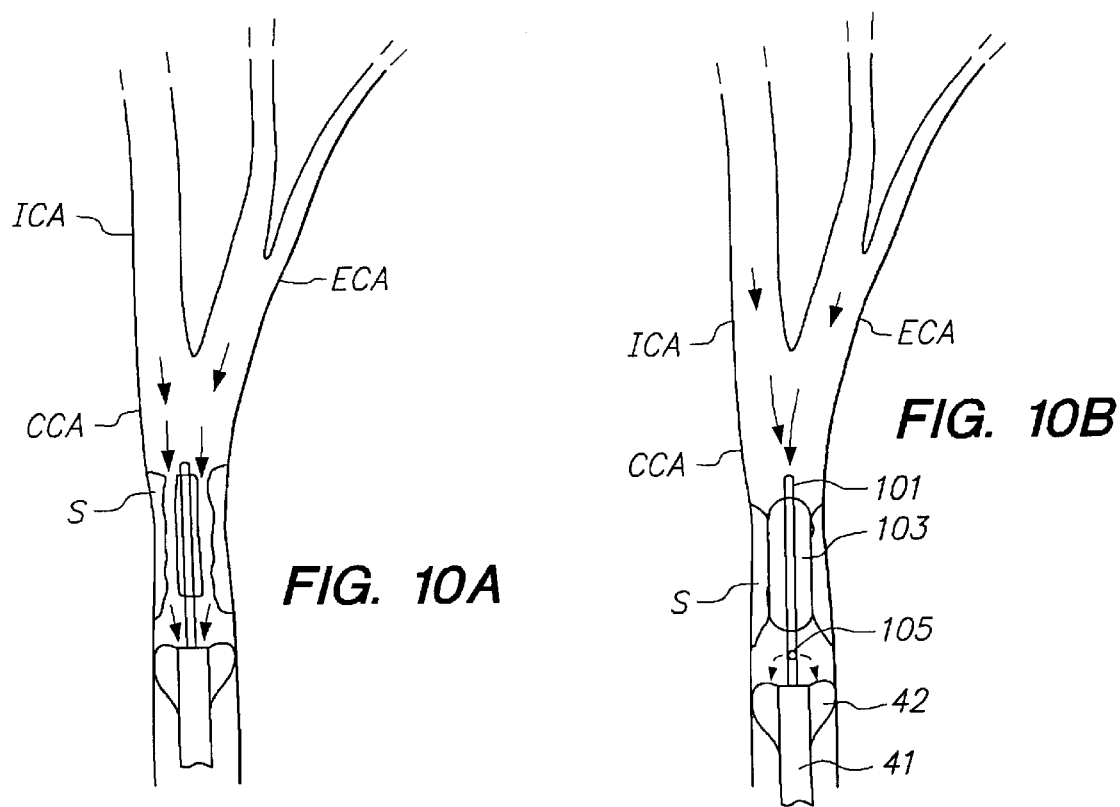
*FIG. 10A*
*FIG. 10B*

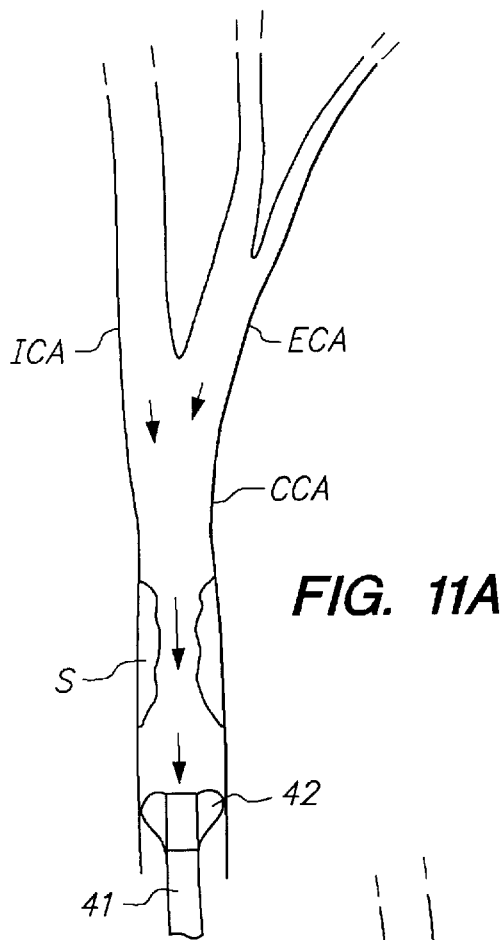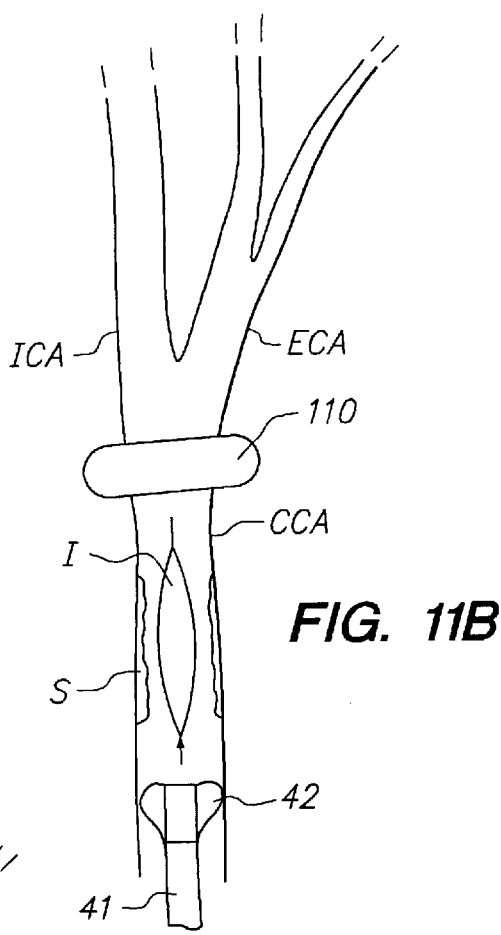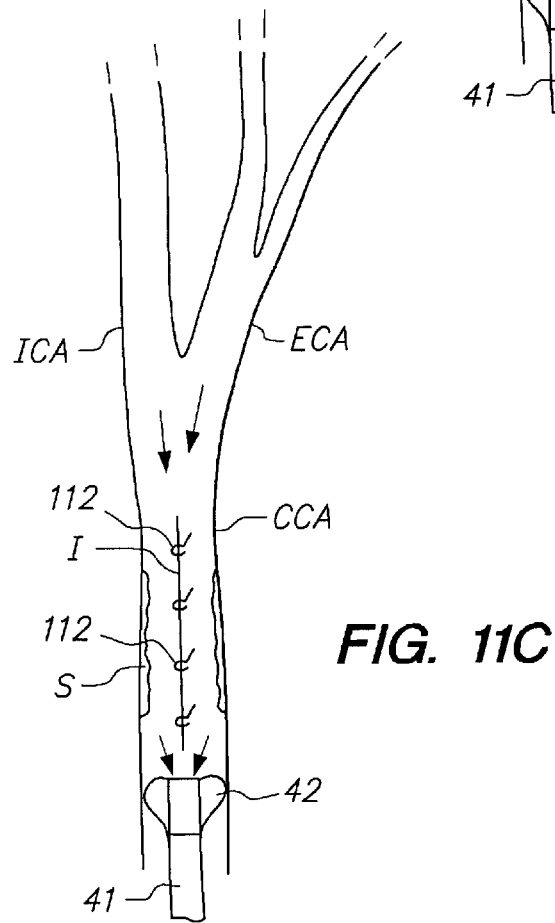

US 6,206,868 B1

PROTECTIVE DEVICE AND METHOD AGAINST EMBOLIZATION DURING TREATMENT OF CAROTID ARTERY DISEASE

REFERENCE TO RELATED APPLICATIONS

The present application is a continuation-in-part of International Application PCT/US99/05469, filed Mar. 12, 1999, which is a continuation-in-part of U.S. patent application Ser. No. 09/078,263, filed May 13, 1998.

FIELD OF THE INVENTION

This invention relates to apparatus and method to protect against embolization during vascular interventions, such as carotid artery angioplasty and endarterectomy. More particularly, the apparatus and methods of the present invention induce retrograde flow in the vessel of interest by providing intermittent suctioning of blood from the vessel of interest at key stages of the procedure.

BACKGROUND OF THE INVENTION

Carotid artery stenoses typically manifest in the common carotid artery, internal carotid artery or external carotid artery as a pathologic narrowing of the vascular wall, for example, caused by the deposition of plaque, that inhibits normal blood flow. Endarterectomy, an open surgical procedure, traditionally has been used to treat such stenosis of the carotid artery.

A important problem encountered in carotid artery surgery is that emboli may be formed during the course of the procedure, and these emboli can rapidly pass into the cerebral vasculature and cause ischemic stroke. Consequently, surgical procedures such as endarterectomy typically have high mortality rates.

In view of the trauma and long recuperation times generally associated with open surgical procedures, considerable interest has arisen in the endovascular treatment of carotid artery stenosis. In particular, widespread interest has arisen in transforming interventional techniques developed for treating coronary artery disease, such as angioplasty and stenting, for use in the carotid arteries. Such endovascular treatments, however, are especially prone to the formation of emboli.

Such emboli may be formed, for example, when an interventional instrument, such as a guide wire or angioplasty balloon, is forcefully passed into or through the stenosis, as well as after dilatation and deflation of the angioplasty balloon or stent deployment. Because such instruments are advanced into the carotid artery from a direction "upstream" of the direction of blood flow, emboli generated by operation of the instruments are carried "downstream" by normal antegrade blood flow—directly into the brain.

Several previously known apparatus and methods attempt to removing emboli formed during endovascular procedures by trapping or suctioning the emboli out of the vessel of interest. These previously known systems, however, provide less than optimal solutions to the problems of effectively removing emboli.

Solano et al. U.S. Pat. No. 4,921,478 describes cerebral angioplasty methods and devices wherein two concentric shafts are coupled at a distal end to a distally-facing funnel-shaped balloon. A lumen of the innermost shaft communicates with an opening in the funnel-shaped balloon at the distal end, and is open to atmospheric pressure at the proximal end. In use, the funnel-shaped balloon is deployed proximally (in the direction of flow) of a stenosis, occluding antegrade flow. An angioplasty balloon catheter is passed through the innermost lumen and into the stenosis, and then inflated to dilate the stenosis. The patent states that when the angioplasty balloon is deflated, a pressure differential between atmospheric pressure and the blood distal to the angioplasty balloon causes a reversal of flow in the vessel that flushes any emboli created by the angioplasty balloon through the lumen of the innermost catheter.

While a seemingly elegant solution to the problem of emboli removal, several drawbacks of the device and methods described in the Solano et al. patent seem to have lead to abandonment of that solution. Chief among these problems is the inability of that system to generate flow reversal during insertion of the guide wire and the angioplasty balloon across the stenosis. Because flow reversal does not occur until after deflation of the angioplasty balloon, there is a substantial risk that any emboli created during placement of the angioplasty balloon will have traveled too far downstream to be captured by the flow reversal. It is expected that this problem is further compounded because only a relatively small volume of blood is removed by the pressure differential induced after deflation of the angioplasty balloon. These same drawbacks appear to have prevented commercialization of a similar system described in EP Publication No. 0 427 429.

Kletschka U.S. Pat. No. 4,794,928 describes an angioplasty device and methods for removing emboli generated during angioplasty, comprising a catheter bundle having an expandable funnel-shaped trap/barrier disposed on its distal end. A removal lumen is situated within the trap/barrier so that a pressure differential generated between the proximal and distal ends causes the emboli to be removed from the trap/barrier. While the patent states that the funnel-shaped trap/barrier may be placed either proximal or distal to the stenosis, the patent illustrates the trap/barrier as being disposed in the direction of antegrade flow, and does not suggest causing flow reversal within a vessel.

Imran U.S. Pat. No. 5,833,650 describes a system for treating stenoses that comprises three concentric shafts. The outermost shaft includes a proximal balloon at its distal end that is deployed proximal of a stenosis to occlude antegrade blood flow. A suction pump then draws suction through a lumen in the outermost shaft to cause a reversal of flow in the vessel while the innermost shaft is passed across the stenosis. Once located distal to the stenosis, a distal balloon on the innermost shaft is deployed to occlude flow distal to the stenosis. Autologous blood taken from a femoral artery using an extracorporeal blood pump is infused through a central lumen of the innermost catheter to provide continued antegrade blood flow distal to the distal balloon. The third concentric shaft, which includes an angioplasty balloon, is then advanced through the annulus between the innermost and outermost catheters to dilate the stenosis.

Like the device of the Solano patent, the device of the Imran patent appears to suffer the drawback of potentially dislodging emboli that is carried into the cerebral vasculature. In particular, once the distal balloon of Imran's innermost shaft is deployed, flow reversal in the vasculature distal to the distal balloon ceases, and the blood perfused through the central lumen of the innermost shaft establishes antegrade flow. Importantly, if emboli are generated during deployment of the distal balloon, those emboli will be carried by the perfused blood directly into the cerebral vasculature, and again pose a risk of ischemic stroke. Moreover, there is some evidence that reperfusion of blood under pressure through a small diameter catheter may contribute to hemolysis and possible dislodgment of emboli.

In view of these drawbacks of the previously known emboli removal systems, it would be desirable to provide methods and apparatus that establish retrograde flow in a vessel at key stages throughout a surgical or interventional procedure, thereby reducing the risk that emboli are carried downstream.

It also would be desirable to provide emboli removal methods and apparatus that ensure that an adequate volume of blood is removed from the system to enhance the likelihood that emboli generated by a surgical or interventional procedure are effectively removed from the vessel of interest.

It still further would be desirable to provide emboli removal methods and apparatus that intermittently provide regional reversal of flow in a vessel, and thus avoid deployment of balloons or other devices distal to the stenosis to delimit a confined treatment field.

SUMMARY OF THE INVENTION

In view of the foregoing, it is an object of this invention to provide emboli removal methods and apparatus that establish retrograde flow in a vessel at key stages throughout a surgical or interventional procedure, thereby reducing the risk that emboli are carried downstream.

It is another object of the present invention to provide emboli removal methods and apparatus that ensure that an adequate volume of blood is removed from the system to enhance the likelihood that emboli generated by a surgical or interventional procedure are effectively removed from the vessel of interest.

It is also an object of this invention to provide emboli removal methods and apparatus that intermittently provide regional reversal of flow in a vessel, and thus avoid deployment of balloons or other devices distal to the stenosis to delimit a confined treatment field.

The foregoing objects of the present invention are accomplished by providing a catheter, an occlusion element disposed on a distal end of the catheter, a suction device, and an aspiration lumen communicating therebetween. The occlusion element is configured to be placed proximal of a stenosis and expanded to occlude antegrade flow, so that flow is reversed in the vessel when the suction device is activated. The aspiration lumen is sized so that an interventional device, such as an angioplasty catheter, may be readily advanced therethrough to the site of a stenosis. The suction device may be activated intermittently to provide reverse flow through the vessel at several stages of the procedure.

In a first preferred embodiment of the present invention, a controller is provided that monitors balloon inflation pressure and restores suction through the aspiration lumen when the pressure falls below a threshold value. In an alternative embodiment, circuitry is provided that monitors the rate of flow through the aspiration lumen, terminates or reduces suction when the flow rate falls below a threshold value, and restores suction through the aspiration lumen when the flow rate of blood through the aspiration lumen exceeds the threshold value. In still other embodiments, the controller may comprise a manually actuated footpedal or handpiece.

In yet another embodiment of the present invention, the emboli removal catheter includes bypass holes that draw blood from a location proximal of the occlusion element when the angioplasty balloon is fully inflated, thus permitting a longer periods of suction and providing some antegrade flow during the non-suction periods. In still other embodiments, the catheter on which the angioplasty balloon is disposed may include bypass lumens that permit reverse flow in the lumen to be established distal to the angioplasty balloon during suction intervals, and antegrade flow at other times.

Methods of using the apparatus of the present invention also are described, in which the catheter is surgically or percutaneously inserted so that the occlusion element is disposed proximal to a stenosis. Suction is drawn at least intermittently through an aspiration lumen of the catheter to induce reverse flow in the vessel at critical stages throughout the procedure, such as during initial placement of a guide wire or angioplasty catheter across a stenosis, and when an angioplasty balloon is cyclically inflated and deflated.

BRIEF DESCRIPTION OF THE DRAWINGS

Further features of the invention, its nature and various advantages will be more apparent from the accompanying drawings and the following detailed description of the preferred embodiments, in which:

FIGS. 3A–3D are, respectively, a schematic view, and detailed side and sectional views of the distal end of an emboli removal catheter of the present invention;

FIGS. 4A and 4B are views of the distal end of an alternative emboli removal catheter suitable for use in the system of FIGS. 3;

FIGS. 5A–5C illustrate a method of using the system of FIGS. 3;

FIGS. 9A and 9B are, respectively, a schematic view and detailed view of the distal end of a further alternative embodiment of the present invention;

FIGS. 10A and 10B illustrate a method of using the system of FIGS. 9; and

FIGS. 11A–11C illustrate a method of using the emboli removal catheter or the present invention in performing endarterectomy.

DESCRIPTION OF THE PREFERRED EMBODIMENTS

Figure 1A:
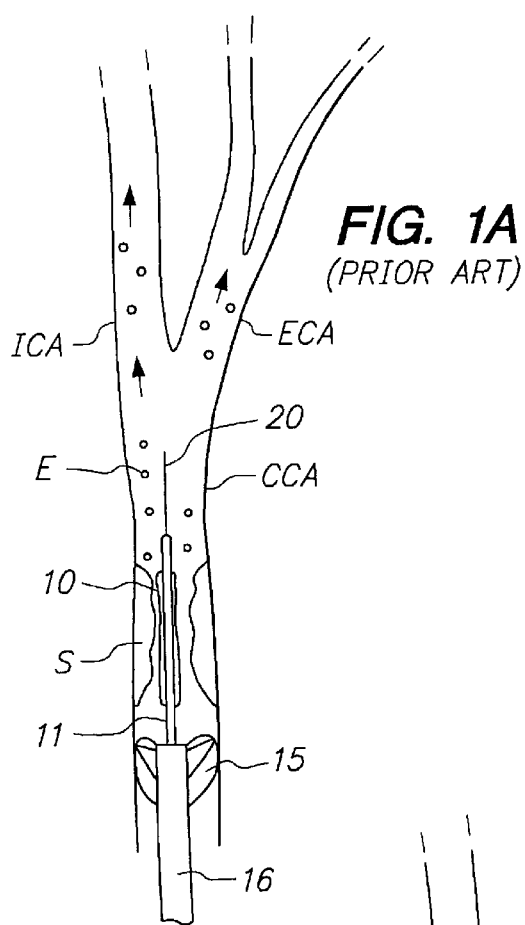
FIGS. 1A and 1B are schematic views of previously known emboli protection systems.
Figure 1B:
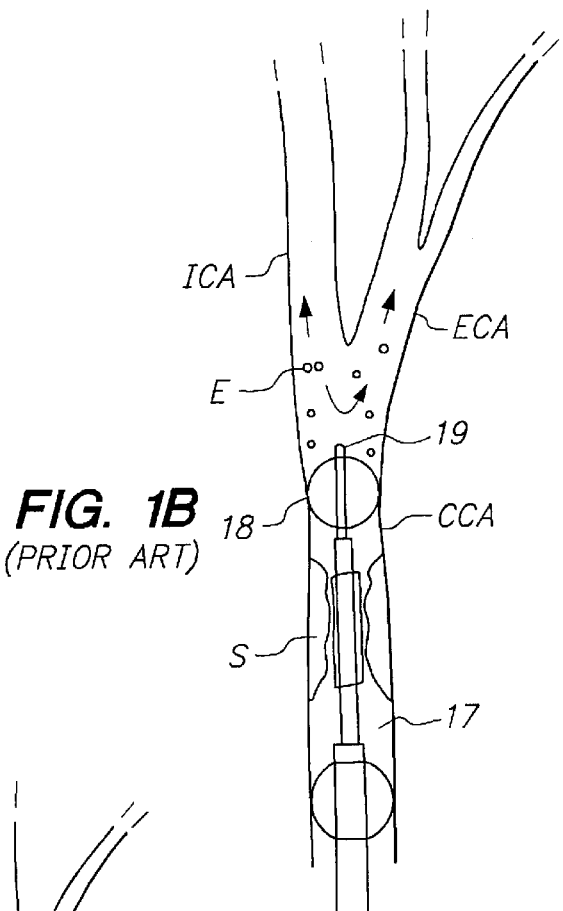

Referring to FIGS. 1A and 1B, drawbacks of previously known emboli removal catheters are described with reference to performing percutaneous angioplasty of stenosis S in common carotid artery CCA. With respect to FIG. 1A, drawbacks associated with naturally-aspirated emboli removal systems, such as described in the above-mentioned patent to Solano and European Patent Publication, are described. No flow reversal is induced by those systems until after balloon 10 of angioplasty catheter 11 first is passed across the stenosis, inflated, and then deflated. Thus, emboli E generated while passing guide wire 20 or catheter 11 across stenosis S may be carried irretrievably into the cerebral vasculature before flow in the vessel is reversed and directed into member 15 of emboli removal catheter 16. Moreover, such naturally-aspirated systems are not expected to cause aspiration of blood at high flow rates sufficiently high to cause regional short-term flow reversal and removal of emboli.

In FIG. 1B, system 17 described in the above-mentioned patent to Imran is shown. As described hereinabove, deployment of distal balloon 18, and ejection of blood out of the distal end of the inner catheter, may cause dislodgement of emboli from the vessel wall distal to balloon 18. The introduction of antegrade flow through inner catheter 19 is expected only to exacerbate the problem by pushing the emboli further into the cerebral vasculature. Thus, applicants expect that while the use of positive suction in the Imran system may remove emboli located in the confined treatment field defined by the proximal and distal balloons, such suction is expected to provide no benefit for emboli dislodged distal of distal balloon 19.

Moreover, the Imran system is incapable of providing "regional" reversal of flow in the vessel once the distal balloon is deployed. In the context of the present invention "regional" reversal of flow means flow in regions distal to the stenosis, as opposed to flow within a confined field, such as delimited by the proximal and distal balloons of the Imran system.

Figure 2:
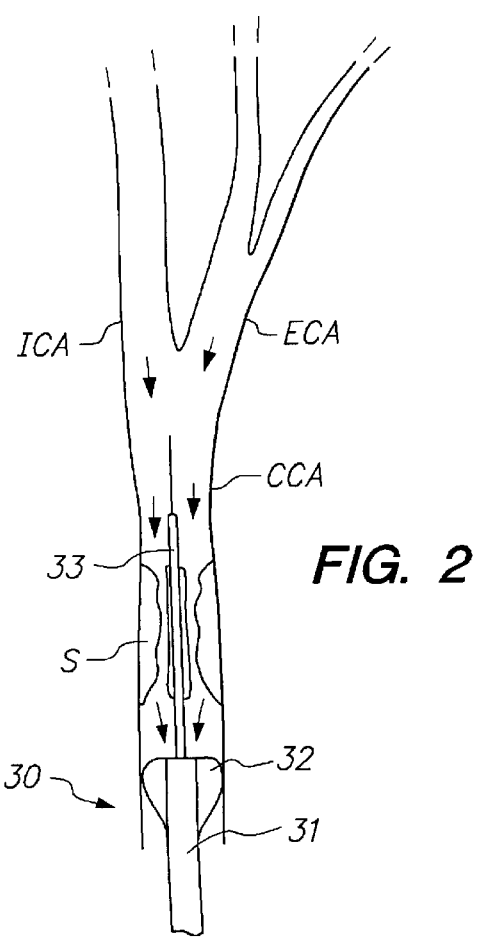
FIG. 2 is a schematic view of the emboli protection system of the present invention.

Referring now to FIG. 2, apparatus and methods of the present invention are described. Apparatus 30 comprises catheter 31 having occlusion element 32 and an aspiration lumen that is coupled to a suction device (see FIG. 3A). In accordance with the principles of the present invention, the aspiration lumen of catheter 31 is coupled to a suction device just before or soon after deploying occlusion element 32, thus inducing reversed flow in the vessel. Illustratively, angioplasty balloon catheter 33 then is inserted through a lumen of catheter 31 and disposed across the lesion. Because flow through the vessel is towards catheter 31, any emboli dislodged by advancing a guide wire or angioplasty catheter 33 across stenosis S causes the emboli to be aspirated by catheter 31.

Unlike the previously-known naturally-aspirated systems, the present invention intermittently induces and maintains flow reversal at key stages throughout the procedure, such as prior to deployment of the occlusion element and when the stenosis is initially traversed. In addition, the methods and apparatus of the present invention rely in part on redistribution of flow through the Circle of Willis to perfuse regions distal to the stenosis, rather by providing antegrade flow distal to an occluding balloon. In this manner the risk of flushing any emboli generated by the use of a distal balloon, as in the above-mentioned Imran system, is significantly reduced.

Referring now to FIGS. 3A to 3C, embolic protective system 40 constructed in accordance with the present invention is described. System 40 comprises emboli removal catheter 41 having distal occlusion element 42, proximal hemostatic port 43, aspiration port 44 and inflation port 45, suction device 46 coupled to aspiration port 44 via hose 47, and controller 48 coupled to pressure sensor 49 and suction device 46. Pressure sensor 49 is located in a T-fitting that configured to be coupled between inflation port 50 of conventional angioplasty catheter 51 and the inflation mechanism, e.g., syringe, (not shown) used to inflate balloon 52 of angioplasty catheter 51. Suction device 46, which also may be manually operated by foot pedal 53 or a handpiece (not shown), and angioplasty catheter 51, may comprise a previously-known, commercially available components. Alternatively, suction device 46 may comprise any other suitable mechanism for drawing a suction through catheter 41, such as a vacuum canister or syringe.

In FIGS. 3B and 3C, distal occlusion element 42 comprises expandable bell or pear-shaped balloon 55. In accordance with manufacturing techniques which are known in the art, balloon 55 comprises a compliant material, such as polyurethane, latex or polyisoprene which has variable thickness along its length to provide a bell-shape when inflated. Balloon 55 is affixed to distal end 56 of catheter 41, for example, by gluing or a melt-bond, so that opening 57 in balloon 55 leads into lumen 58 of catheter 41. Balloon 55 preferably is wrapped and heat treated during manufacture so that distal portion 59 of the balloon extends beyond the distal end of catheter 41 and provides an atraumatic tip or bumper for the catheter.

As shown in FIG. 3C, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 45 to balloon 55. In a preferred embodiment of catheter 41, the diameter of lumen 58 is 7 Fr, and the outer diameter of the catheter is approximately 9 Fr.

Controller 48 preferably includes circuitry or programming that interprets the signal generated by pressure sensor 49 and controls actuation of suction device 46 responsive to the measured pressure. More specifically, the T-fitting housing pressure sensor 49 is configured to be coupled between angioplasty catheter 51 and an inflation mechanism, such as a syringe or piston. Pressure sensor 49 outputs a signal corresponding to the inflation pressure applied to balloon 55.

Controller 48 may be designed or programmed to detect when the pressure signal output by sensor 49 exceeds a predetermined value corresponding to dilation of the angioplasty balloon 52, and terminate or reduce suction through catheter 41, e.g., either by shutting off suction device 46 or opening the inlet to the suction device to atmospheric pressure. When controller 48 subsequently detects a pressure signal from sensor 49 indicating that the inflation pressure has fallen below the predetermined value, corresponding to deflation of balloon 55, controller briefly restores suction to lumen 58 of catheter 41, thus causing any emboli generated by actuation of balloon 55 to be aspirated through lumen 58.

Alternatively, suction device 46 may be selectively actuated by the physician at desired stages of the procedure by manually depressing footpedal 53. As a yet further alternative, footpedal 53 may be coupled to controller 48, and the controller may include timer circuitry or programming that actuates suction device 46 for a user-selectable interval once the footpedal is depressed.

Referring now to FIGS. 5A to 5C, use of the apparatus of FIG. 2 in accordance with the methods of the present invention is described. In FIGS. 5, stenosis S is located in the common carotid artery below the bifurcation between internal carotid artery ICA and external carotid artery ECA. In a first step, catheter 41 is inserted, either percutaneously and transluminally or via a surgical cut-down, to a position proximal of stenosis S, without causing guide wire 20 to cross the stenosis. Balloon 55 is inflated, preferably with a radioopaque contrast solution, via inflation port 45. Suction device 46 preferably is actuated to establish retrograde flow in the artery just prior to deployment of balloon 55, so that any emboli generated by deployment of the balloon will be removed through lumen 58 of catheter 41. Alternatively, suction device 46 may be actuated just after balloon 55 is deployed.

Suction then is maintained for the duration of the following step, a period of about 10 seconds. As depicted in FIG. 5B, guide wire 20 is advanced across the stenosis, as determined, for example, by fluoroscopy. Throughout this step of placing the guide wire, retrograde flow, for example, as may be determined using a Doppler ultrasound monitor, is maintained through the arteries ICA and ECA and into lumen 58 of catheter 41.

Angioplasty catheter 51 illustratively is advanced along guide wire 20 through hemostatic port 43 and aspiration lumen 58 of catheter 41 until it is disposed across the stenosis. Throughout this step of placing the angioplasty catheter across the stenosis, generally about 15 to 20 seconds, suction device 46 is activated to drain blood and any emboli generated from the artery through aspiration lumen 58. Once again, a Doppler monitor may be used to confirm that flow distal to the stenosis has been reversed.

Pressure sensor 49 then is coupled in the inflation circuit of the angioplasty catheter, and a desired inflation pressure is preset or input into controller 48 via an appropriate input device, i.e., keypad. Balloon 52 is inflated to or beyond the desired inflation pressure to disrupt the plaque constituting the stenosis. When angioplasty balloon 52 is subsequently deflated, pressure sensor 49 detects that reduction in inflation pressure, and controller 48 restores suction through lumen 58 for about 10 to 30 seconds to aspirate the blood distal to the balloon. Controller 48 thus triggers suction device 46 to induce retrograde flow of blood through the artery to remove any emboli generated during operation of the angioplasty catheter, as depicted in FIG. 5C.

Alternatively, the physician may use footpedal 53 to reestablish suction for a selected interval. As is typical of angioplasty procedures, the steps of inflating and deflating the angioplasty balloon, and inducing reverse flow in the artery after each inflation cycle, may be repeated. Similar steps may be employed during subsequent deployment of a stent, if desired.

Preferably, regional reversal of blood flow is established only intermittently and for brief periods during the procedure. Although it is possible to sustain continuous reverse flow throughout the procedure, such sustained reverse flow may be less preferred as potentially depriving the brain of oxygen. Thus, in the preferred embodiment, during each stage of a procedure that could dislodge emboli, reverse flow is initiated only so long as needed to ensure that potential emboli have been removed. The suction periods described hereinabove are representative of periods believed useful in practice, but shorter or longer periods may be necessary or useful in a particular procedure or type of procedure or for a particular patient.

It is expected that the method of the present invention typically will result in the drainage of approximately 300 cc of blood, but the amount of blood drained may vary. If desired, the aspirated blood may be cleansed and intravenously reperfused to the patient using a previously known extracorporeal blood filter and pump.

As set forth above, the method of the present invention protects against embolization by reversing the blood of flow in the brain distal to the stenosis at key stages during a carotid angioplasty procedure. The total period of reversal of blood flow in the brain distal to the stenosis preferably should have a duration of about one minute. In a typical patient, blood flow may be reversed for up to approximately three minutes before there is likely to be any danger from ischemia. Less than five percent of patients are likely to have an anomalous insufficiency of segments of the Circle of Willis that reduces collateral flow, but even these patients are expected to tolerate flow reversals lasting a minute or less.

Referring now to FIGS. 4A and 4B, an alternative embodiment of occlusion element 42 of the system of FIG. 3A is described. In FIGS. 4A and 4B, occlusion element 42 of emboli removal catheter 41 comprises self-expanding wire mesh basket 65 covered with elastomeric polymer 66, such as latex, polyurethane or polyisoprene. Alternatively, a tightly knit self-expanding wire mesh may be used, with or without an elastomeric covering.

Catheter 41 is surrounded by movable sheath 67. Catheter 41 is inserted transluminally with sheath 67 in a distalmost position, and after basket 65 has been determined to be in a desired position proximal to a stenosis, sheath 67 is retracted proximally to cause basket 65 to deploy. Upon completion of the procedure, basket 65 is again collapsed within sheath 67 by moving the sheath to its distalmost position. Operation of the system of FIG. 3A using the emboli removal catheter of FIGS. 4A and 4B is similar to that described for FIGS. 5A–5C, except that the occlusion element self-expands when sheath 67 is retracted, rather than by infusing an inflation medium to balloon 55.

Figure 6:
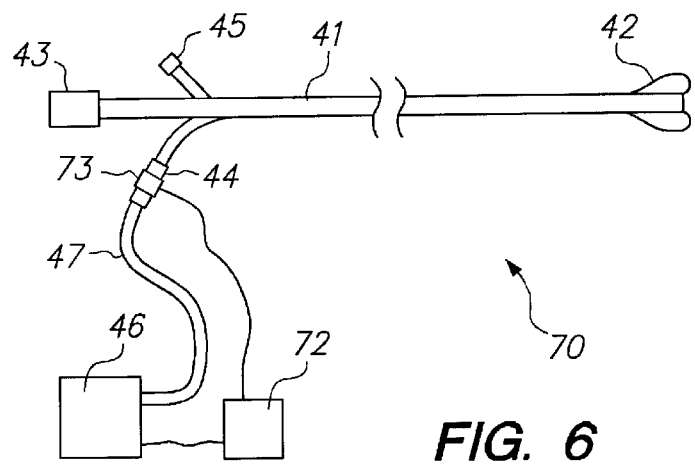
FIG. 6 is a schematic view of an alternative embodiment of the invention of FIGS. 3.

Referring to FIG. 6, another alternative embodiment of the present invention is described. Emboli removal system 70 comprises emboli removal catheter 41 and suction device 46 identical to that described hereinabove with respect to FIG. 3A. Controller 72 is coupled to flow rate sensor 73, which is housed in a coupling configured to be disposed between aspiration port 44 and hose 47. Flow rate sensor monitors the flow of blood through aspiration lumen 58. Controller 72 includes circuitry or programming to terminate suction through catheter 41 when the rate falls below a user selected value, corresponding to the condition where the angioplasty balloon is fully inflated.

Controller 72 also includes circuitry or programming to restore suction to through the aspiration lumen of catheter 41 when the flow rate of blood increases beyond the threshold value, such as when there is a naturally-aspirated surge of blood caused by deflation of the angioplasty balloon. Thus, this embodiment of the present invention takes advantage of the surge of naturally-aspirated blood observed in the foregoing Solano et al. patent as a trigger for actuating the suction device for a user selected period, such as 15 to 30 seconds. Operation of system 70 is otherwise the same as described hereinabove with respect to FIGS. 5.

Figure 7A:
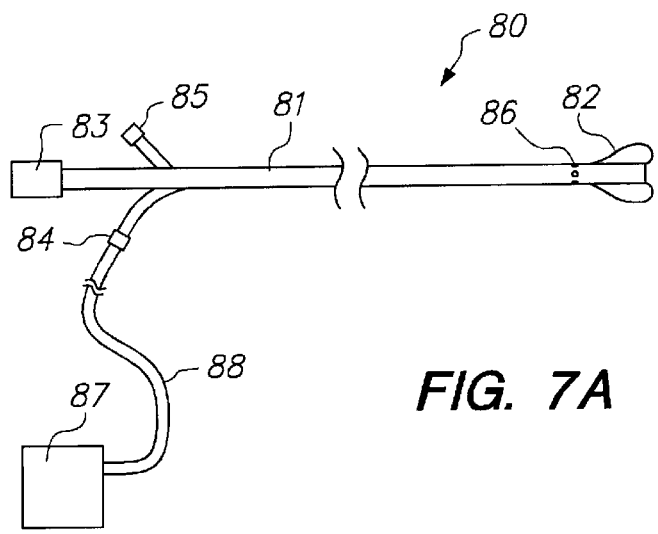
FIGS. 7A–7C are, respectively, a schematic view, and detailed views of the distal end of another alternative embodiment an emboli removal catheter of the present invention.
Figure 7B:
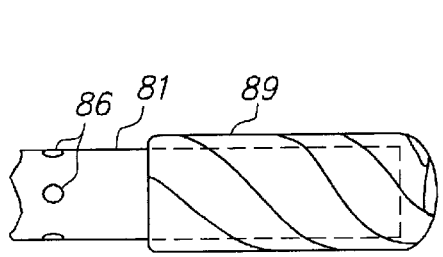
Figure 7C:
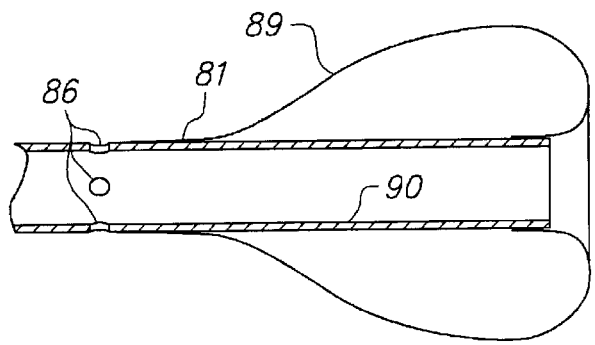

In FIGS. 7A–7C, yet another alternative embodiment of the present invention is described. Emboli removal system 80 includes catheter 81 having occlusion element 82, proximal hemostatic port 83, aspiration port 84, inflation port 85, and one or more bypass holes 86 located just proximal of occlusion element 82. Suction device 87 is coupled to aspiration port 83 via hose 88, and may be actuated by a foot pedal (not shown). Catheter 81 preferably is used in conjunction with an angioplasty balloon catheter such as shown in FIG. 3A or a suitable stent deployment system.

The distal end of catheter 81 differs in construction from that described above with respect to FIGS. 3B and 3C only in that catheter 81 includes one or more through-wall bypass holes 86. Bypass holes 86 permit blood to pass from a location proximal to occlusion element 82 (illustratively balloon 89) and into aspiration lumen 90 to limit the maximum suction level applied to the vessel wall section disposed between the occlusion element and the angioplasty balloon. Catheter 81 is otherwise constructed as described above for catheter 41 of FIGS. 3.

Figure 8A:
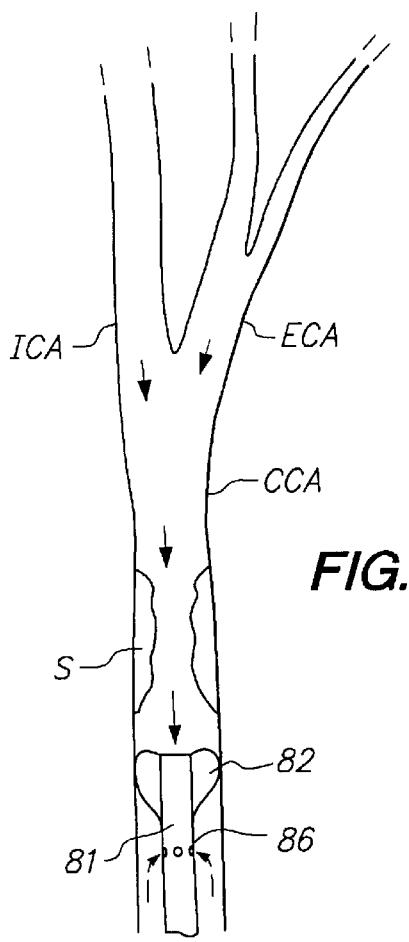
FIGS. 8A–8C illustrate a method of using the system of FIGS. 7 in accordance with the principles of the present invention.
Figure 8B:
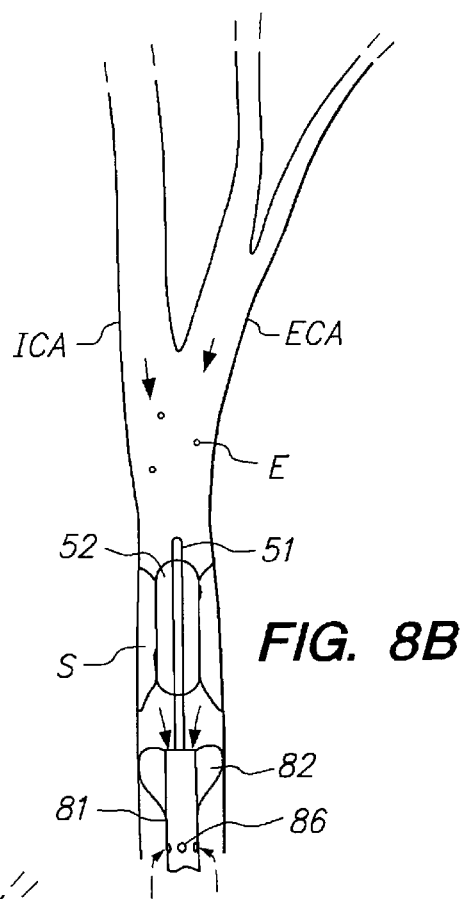
Figure 8C:
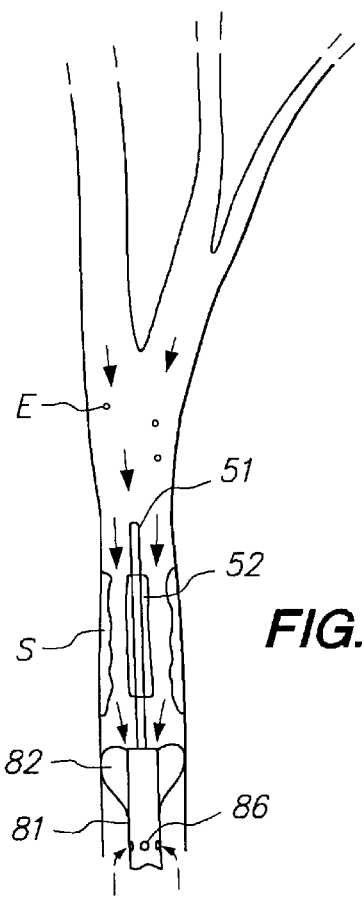

Referring to FIGS. 8A–8C, methods of using the apparatus of FIGS. 7 are described. In FIG. 8A, catheter 81 is first inserted either surgically or percutaneously and transluminally to a position proximal of stenosis S. Occlusion element 82 is deployed while suction device 87 is actuated for 10–15 seconds to induce retrograde flow through the stenosis. Because aspiration lumen 90 is unblocked, only a small fraction of blood will be drawn through bypass holes 86.

In FIG. 8B, balloon 52 of angioplasty catheter 51 is shown fully inflated, so that it occludes the vessel distal to the stenosis. In this case, once the supply of blood captured between occlusion element 82 and angioplasty balloon 52 is reduced, proportionately more blood will be drawn through bypass holes. This is expected to advantageously reduce the stress applied to the section of vessel wall between occlusion element 82 and the stenosis, thus reducing the risk of narrowing or collapsing the vessel.

With respect to FIG. 8C, once balloon 52 of the angioplasty catheter is deflated, the blood drained through aspiration lumen 90 again will consist mostly of blood drawn in a retrograde manner through the vessel, with a small proportion coming through bypass holes 86. Accordingly, it is contemplated that the bypass holes employed in catheter 81 will enable suction to be used for longer periods of time while posing a smaller risk of injury to the vessel wall.

It is expected that the longer duration and larger volume of retrograde blood flow in and around the region of stenosis enabled by providing bypass holes 86 may allow for the removal of plaque and debris that lower blood volumes may not be able to remove. Bypass holes 86 also may reduce thrombus formation proximal to occlusion element 82 by providing for continuous suction of emboli from the vessel. In addition, bypass holes 86 may be beneficial patients with reduced collateral blood flow by allowing antegrade blood flow during those periods when suction is not applied to the aspiration lumen (and the angioplasty balloon is not fully inflated). Alternatively, or in addition, catheter 81 may be advantageously used with any of the occlusion elements or controllers described in the preceding embodiments.

Referring to FIGS. 9A and 9B, another alternative embodiment of the present invention is described. System 100 comprises emboli removal catheter 41 coupled to suction device 46 via hose 47, wherein all of the components are identical to those described hereinabove with respect to FIGS. 3, and angioplasty catheter 101. Angioplasty catheter 101 includes luer 102 having a hemostatic seal, balloon 103, guide wire lumen 104, and bypass holes 105. Bypass holes 105 communicate with guide wire lumen 104, which in turn terminates in an opening (not visible) in distal face 106 of catheter 101.

Operation of system 100 is described with respect to FIGS. 10A and 10B. In FIG. 10A, catheter 41 is either surgically or percutaneously and transluminally deployed as described above with respect to FIG. 5A. Angioplasty catheter 101 then is advanced across stenosis S while suction is drawn through catheter 41.

Balloon 103 is inflated to disrupt the stenosis. As balloon 103 is initially inflated, suction device 46 is activated to cause blood to flow through the opening in the distal end of angioplasty catheter 101 and through bypass holes 105, thereby inducing retrograde flow in the vessel distal to the inflated angioplasty balloon. This flow advantageously is expected to remove any emboli generated distal to the distal face of balloon 103 by first drawing such emboli into through the bypass holes into the space defined by the balloon 103 and occlusion element 42. The emboli will then be removed from that space through aspiration lumen 58 of catheter 41.

Alternatively, if angioplasty catheter 101 is used in conjunction with emboli removal catheter 81 of FIGS. 7, the combination of bypass holes 103 and 86 will provide some antegrade flow distal to the stenosis when suction device 46 is not active, even when the angioplasty balloon is fully inflated. This feature may be particularly beneficial in those situations where it is desired to leave the angioplasty balloon inflated for several minutes at a time. Importantly, such a combination provides the capability not only to provide antegrade flow, but also the ability to remove emboli generated distal to the distal surface of the angioplasty balloon.

In FIGS. 11A to 11C, methods of using the emboli removal catheter of FIGS. 3A, 6 and 7 during endarterectomy is described. In FIG. 11A, catheter 41 is either surgically or percutaneously and transluminally inserted into common carotid artery CCA proximal to stenosis S. Suction is then drawn with suction device 46 while occlusion element 42 is deployed.

In FIG. 11B, cross clamp 110 is applied to common carotid artery CCA proximal of the bifurcation between internal carotid artery ICA and external carotid artery ECA, and lengthwise incision I is formed through which the stenosis is removed by means which are per se known. In FIG. 11C, after incision I is closed, illustratively using sutures 112, suction device 46 is again actuated while cross-clamp 110 is removed. In this manner, any emboli dislodged from the wall of the vessel or by removal of cross-clamp 110 will be removed by the regional reversal of flow to catheter 41. After suction device has been operated for about 10–30 seconds, suction is discontinued and the emboli removal device is removed.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A method for removing emboli from a vessel during treatment of a stenosis, the method comprising:

providing an emboli removal catheter having proximal and distal ends, a lumen extending therethrough, an occlusion element disposed on the distal end, and a suction device coupled to the lumen;

providing an angioplasty catheter having a balloon;

inserting the distal end of the emboli removal catheter transluminally to a position proximal to the stenosis;

deploying the occlusion element to occlude antegrade flow through the vessel;

actuating the suction device to induce reverse flow in the vessel;

while flow is reversed in the vessel, advancing the balloon of the angioplasty catheter across the stenosis;

actuating the balloon of the angioplasty catheter to dilate the stenosis; and when the balloon of the angioplasty catheter is deflated, actuating the suction device to induce regional reversal of flow in the vessel to remove emboli generated by actuating the balloon.

2. The method of claim 1 wherein the occlusion element comprises a balloon, and deploying the occlusion element comprises inflating the balloon.

3. The method of claim 1 wherein the occlusion element comprises a self-expanding basket, and deploying the occlusion element comprises retracting a sheath relative to the distal end of the emboli removal catheter.

4. The method of claim 1 wherein advancing the balloon of the angioplasty catheter across the stenosis further comprises advancing the angioplasty catheter through the lumen of the emboli removal catheter.

5. The method of claim 1 further comprising:

providing a pressure sensor;

coupling the pressure sensor to the angioplasty catheter;

detecting an inflation pressure in the balloon of the angioplasty catheter; and actuating the suction device responsive to the detected inflation pressure.

6. The method of claim 1 further comprising:

providing a flow sensor;

coupling the flow sensor to the lumen of the emboli removal catheter;

detecting a flow rate in the lumen; and actuating the suction device responsive to the detected flow rate.

7. The method of claim 1 wherein the emboli removal catheter further comprises at least one through-wall bypass hole disposed in the emboli removal catheter proximal of the occlusion element, the method further comprising suctioning blood through the bypass hole when the balloon of the angioplasty catheter is fully inflated.

8. The method of claim 7 further comprising passing blood through the bypass hole to provide antegrade flow in the vessel when the balloon of the angioplasty catheter is deflated.

9. The method of claim 1 wherein the angioplasty catheter further comprises a guide wire lumen and at least one through-wall bypass hole that communicates with the guide wire lumen, the method further comprising suctioning blood through the guide wire lumen and bypass hole to induce reverse flow in the vessel distal to the balloon of the angioplasty catheter when the balloon of the angioplasty catheter is fully inflated.

10. The method of claim 9 further comprising passing blood through the bypass hole and guide wire lumen to provide antegrade flow in the vessel, distal to the balloon of the angioplasty catheter, when the suction device not actuated.

* * * * *